United States Patent [19]

Denis et al.

[11] Patent Number: 5,587,056
[45] Date of Patent: Dec. 24, 1996

[54] SEPARATION OF ALIPHATIC DIACIDS FROM ADIPIC ACID ADMIXTURES THEREOF

[75] Inventors: Philippe Denis, Decines; Carl Patois, Lyon; Robert Perron, Charly, all of France

[73] Assignee: Rhone-Poulenc Chimie, Courbevoie Cedex, France

[21] Appl. No.: 490,231

[22] Filed: Jun. 14, 1995

[30] Foreign Application Priority Data

Jun. 14, 1994 [FR] France .................................. 94 07505

[51] Int. Cl.$^6$ ...................................................... B01D 3/34
[52] U.S. Cl. ................... 203/29; 203/34; 203/35; 203/48; 562/593
[58] Field of Search ............................... 203/29, 34, 35, 203/38, 48, 51, 52; 210/767; 562/590, 593, 512.4, 523

[56] References Cited

U.S. PATENT DOCUMENTS

| 3,957,830 | 5/1976 | Mesch et al. | 203/15 |
| 4,191,616 | 3/1980 | Baker | 203/44 |
| 4,230,887 | 10/1980 | Mitchell et al. | 562/593 |
| 5,292,944 | 3/1994 | Atadan et al. | 562/590 |

FOREIGN PATENT DOCUMENTS

| 1316914 | 4/1963 | France . |
| 1938103 | 1/1971 | Germany . |

*Primary Examiner*—Robert J. Warden
*Assistant Examiner*—Robert Carpenter
*Attorney, Agent, or Firm*—Burns, Doane, Swecker & Mathis, L.L.P.

[57] ABSTRACT

At least a fraction of at least one branched, saturated aliphatic diacid having 6 carbon atoms, for example 2-methylglutaric acid and/or 2-ethylsuccinic acid and/or dimethylsuccinic acid, is separated from admixtures thereof with adipic acid, by at least partially converting such at least one aliphatic diacid into the corresponding anhydride thereof, and removing the corresponding anhydride or the adipic acid from the medium of conversion/anhydridization, for example by contemporaneous or subsequent distillation, or by crystallization.

22 Claims, No Drawings

5,587,056

SEPARATION OF ALIPHATIC DIACIDS FROM ADIPIC ACID ADMIXTURES THEREOF

BACKGROUND OF THE INVENTION

1. Technical Field of the Invention

The present invention relates to the separation of at least one aliphatic diacid from immixtures thereof with adipic acid.

2. Description of the Prior Art

Adipic acid is one of the two basic starting materials for the production of nylon-66 (polyamide-66).

Various processes are known to this art for the preparation of adipic acid, certain of which are industrial and others are at the research or development stage.

One process described in the patent literature entails hydroxycarbonylating butadiene into pentenoic acids, and then hydroxycarbonylating said pentenoic acids into adipic acid. During the second hydroxycarbonylation reaction, methylglutaric acid, ethylsuccinic acid and dimethylsuccinic acid are also formed, in amounts which vary depending on the conditions under which the process is carried out.

These various branched saturated aliphatic diacids may be upgradable to a greater or lesser extent, but it is important in each instance to separate them as completely as possible from the adipic acid, which remains, both qualitatively and quantitatively, the most commercially important compound.

Processes for fractionating these mixtures can thus be employed, for example by crystallization, to separate the branched diacids from the adipic acid. However, in respect of the adipic acid isomers, this technique does not permit an efficient, easy separation, because of the very close physical properties of all of these diacids.

SUMMARY OF THE INVENTION

Accordingly, a major object of the present invention is the provision of an improved process for the separation of branched, saturated aliphatic diacids containing 6 carbon atoms, from immixtures thereof at least containing adipic acid, by converting at least certain of said diacids into the corresponding anhydrides thereof.

Briefly, then, the present invention features separating at least a portion of one or more branched, saturated aliphatic diacids having 6 carbon atoms, from mixtures comprised thereof with at least adipic acid, comprising at least partially converting said diacid(s) into the corresponding anhydrides thereof and recovering the desired final compounds.

DETAILED DESCRIPTION OF BEST MODE AND PREFERRED EMBODIMENTS OF THE INVENTION

More particularly according to the present invention, the diacid mixtures to be separated include both a single such diacid with adipic acid and mixtures of several such diacids with adipic acid, and may of course also contain other compounds. By the term "diacids" is also intended a single diacid. Similarly, the term "diacids" does not, except where otherwise indicated., encompass adipic acid itself. Lastly, the conversion of the diacids into their respective corresponding anhydrides will hereinafter be referred to as "anhydridization."

The saturated aliphatic diacids according to the process of the invention include 2-methylglutaric acid and/or 2-ethylsuccinic acid and/or, also, dimethylsuccinic acid.

The anhydridization of the saturated aliphatic diacids may be carried out by heating the mixtures comprised thereof to a temperature equal to or above 60° C.

To facilitate the dehydration of the diacids, it is generally preferable to separate, especially by distillation, the anhydrides formed or the water formed, during the anhydrization or subsequent thereto. However, this is not critical and the anhydrides formed may also remain in the reaction medium and may be separated from the adipic acid and from the other compounds present, by any known means such as, for example, a distillation or a crystallization, only during a subsequent operation.

Since the heating and the possible distillation may be carried out at a pressure equal to, above or below atmospheric pressure, the temperature at which the anhydridization will be carried out may vary as a function of this pressure, and as a function of the composition of the mixture to be treated.

However, the process is advantageously carried out at a temperature of 80° C. to 350° C.

The process may advantageously be carried out in the presence of a homogeneous acid catalyst, namely, one which is soluble in the reaction medium, having a pKa below or equal to 5 such as, for example, sulfuric acid, hydriodic acid, para-toluenesulfonic acid, trifluoroacetic acid, or trifluoromethanesulfonic acid, or a heterogeneous acid catalyst such as, for example, boron phosphate, zirconia or sulfonated resins such as those marketed under the trademark Nafion, or, alternatively, acidic clays such as, in particular, smectites such as, for example, montmorillonites, beidellites, nontronites, hectorites, stevensdites and saponites.

The amount of homogeneous or heterogeneous acid catalyst may vary very widely, since the presence of such an acid is not essential. It may thus be present in an amount such that there exists an acid/diacids to be anhydridized molar ratio of from 0 to 10. The homogeneous or heterogeneous acid catalyst is preferably present in an amount such that the acid/diacids to be anhydridized molar ratio ranges from 0.0005 to 1. When a sulfonated acidic resin is used, the molar ratio will be determined based on the sulfonic acid functions of the resin and the diacids to be anhydridized. When an acidic clay is used, an acidic clay/diacids to be anhydridized weight ratio of at least 5% may be used, but it is obvious that this ratio may be very widely varied, depending on the actual operating conditions of the process. In particular, when the process is carried out continuously, the ratio is no longer meaningful and it is the contact time that becomes important.

The process of the invention is also advantageously carried out in the presence, in the reaction medium, of one or more anhydrides, such as the anhydrides of monocarboxylic or polycarboxylic aliphatic acids. It is necessary that the boiling point of these acids be below that of adipic acid (i.e., about 265° C. at 13.3 KPa) in order that the acids formed from the anhydrides thereof be separable by distillation. Such anhydrides are preferably the anhydrides of monocarboxylic or polycarboxylic acids having from 2 to 8 carbon atoms, for example the anhydrides of acetic acid, propionic acid, succinic acid, valeric acid, 2-ethylsuccinic acid, dimethylsuccinic acid, methylbutanoic acids, methylbutenoic acids or pentenoic acids, as well as the mixed anhydrides of these acids.

It will be appreciated that the selection of 2-ethylsuccinic anhydride and dimethylsuccinic anhydride is not in order, if the diacids to be separated from adipic acid are not 2-ethylsuccinic acid and dimethylsuccinic acid, respectively.

In this embodiment, the amount of anhydride optionally added to the reaction medium to facilitate anhydridization of the diacids may vary over a very wide range, since the presence of such a compound is not essential, even though this constitutes a preferred embodiment of the invention. The amount of anhydride may thus be such as to provide an anhydride/diacids to be anhydridized molar ratio of 0 to 10. The molar ratio anhydride/diacids to be anhydridized preferably ranges from 0.5 to 2 and even more preferably from 1 to 1.5.

As indicated above, the diacid mixtures treated in the process of the invention may be mixtures emanating from any origin; in particular, they may originate from the recovery of the diacids in waters of recrystallization of adipic acid, or, alternatively, from the diacid distillation residues. Also, they may comprise more or less pure fractions emanating from crystallization, refining or distillation operations carried out in conjunction with the preparation of adipic acid.

They may also directly originate from processes for the synthesis of adipic acid. This is especially the case in respect of mixtures of adipic acid with 2-methylglutaric acid and/or 2-ethylsuccinic acid and/or dimethylsuccinic acid, which are obtained during the hydroxycarbonylation of pentenoic acids or, where appropriate, even during the hydroxycarbonylation of butadiene or derivatives thereof. These mixtures may also contain, depending on the particular steps of the preparative technique, greater or lesser amounts of the catalyst employed, such as, for example, iridium or iridium compounds, rhodium or rhodium compounds and palladium or palladium compounds, the latter category of catalysts being used, more particularly, for the hydroxycarbonylation of butadiene or derivatives thereof. They may also include compounds such as pentenoic acids, optional solvents, and cocatalysts, as well as compounds formed during the synthesis of adipic acid such as, in particular, valeric acid, methylbutanoic acids, methylbutenoic acids and gamma-valerolactone.

The presence of catalyst, in particular of iridium or iridium compounds, rhodium or rhodium compounds and palladium or palladium compounds, as well as the respective cocatalysts or promoters of these catalysts, may serve a beneficial function in the anhydridization of the diacids. Whether they originate from the reaction mixtures derived from processes for the hydroxycarbonylation of the pentenoic acids or of butadiene, or whether they are optionally introduced before the anhydridization process is carried out, the catalyst constitutes, in moles of metal relative to the moles of diacids to be treated, from 0% to 20%, preferably from 0% to 10% and even more preferably from 0% to 5%.

The amounts of the various compounds indicated above in the reaction media emanating from the hydroxycarbonylation of the pentenoic acids, or of butadiene or derivatives thereof, are not critical. Exemplary such amounts are described in EP-A-0,477,112, EP-A-0,478,472, EP-A-0,493,273, EP-A-0,511,126 and EP-A-0,536,064, each relating to the synthesis of adipic acid.

In the anhydridization process of the invention, a solvent may be added to the mixture of diacids to be separated, which solvent may be added to the mixture of diacids to be separated, which solvent may be one of the compounds indicated above, or may be different from the compounds present in the reaction medium provided via the synthesis of adipic acid and the diacids to be anhydridized.

Particularly exemplary such solvents include aliphatic or cycloaliphatic hydrocarbons, halogenated, in particular chlorinated, aliphatic or cycloaliphatic hydrocarbons, aromatic hydrocarbons, halogenated, in particular chlorinated, aromatic hydrocarbons, aliphatic or aromatic or mixed ethers, carboxylic acids, in particular aliphatic carboxylic acids, and halogenated carboxylic acids.

Specific examples of these solvents are benzene, toluene, xylenes, n-hexane, dichloromethane, 1,2-dichloroethane, cyclohexane, chlorobenzene, diphenyl ether, dibutyl ether, pentenoic acids, valeric acid, gamma-valerolactone, acetic acid, propionic acid and trifluoroacetic acid.

These solvents are added for the purpose of diluting the diacids and promoting their anhydridization. They may also be selected to permit the azeotropic distillation of the water formed during the anhydridization.

The amount of solvent advantageously ranges from 0% to 95% of the total weight of the mixture containing the diacids.

The diacids to be anhydridized typically constitutes from 10% to 90% by weight, relative to the diabids/adipic acid total weight ratio in the mixture to be treated.

The conversion of the diacids into their anhydrides permits the more ready separation thereof from the adipic acid, in particular by distillation. This because of the much lower boiling points of the anhydrides relative to their respective diacids.

In order to further illustrate the present invention and the advantages thereof, the following specific examples are given, it being understood that same are intended only as illustrative and in nowise limitative.

EXAMPLE 1

A mixture containing 50 millimol (mmol) of 2-methylglutaric acid, 25 mmol of adipic acid and 50 mmol of pentenoic acid (serving as solvent) was introduced into a 50 ml glass round-bottomed flask, to which 2 mmol of concentrated sulfuric acid were added.

The mixture was stirred, heated to 130° C. and maintained at this temperature for 30 minutes.

On distillation under reduced pressure (about 1,000 Pa), 80% of the corresponding anhydride was obtained relative to the 2-methylglutaric acid charged.

EXAMPLE 2

The procedure of Example 1 was repeated under the same operating conditions, but the 2-methylglutaric acid was replaced by the same molar amount of 2-ethylsuccinic acid. On distillation, 100% of the corresponding anhydride was obtained relative to the 2-ethylsuccinic acid charged.

EXAMPLE 3

A mixture containing 34 mmol of 2-methylglutaric acid, 39 mmol of 2-ethylsuccinic anhydride and 25 mmol of adipic acid was introduced into a 50 ml glass round-bottomed flask.

The mixture was stirred, heated to 120° C. and maintained at this temperature for one hour. On distillation as in Example 1, 2 mmol of anhydride corresponding to 2-methylglutaric acid were obtained.

EXAMPLE 4

The procedure of Example 1 was repeated under the same operating conditions, but the sulfuric acid was replaced by 2.5 mmol of boron phosphate. On distillation as in Example 1, 9 mmol of anhydride corresponding to 2-methylglutaric acid were obtained.

EXAMPLE 5

The following reagents were successively introduced into a 125 ml autoclave:

(i) 0.8 mmol of RhCl(cod) {cod=1,5-cyclooctadiene}, (ii) 8 mmol of HI (at a concentration of 57% in water), (iii) 45 mmol of water (provided by the HI solution), (iv) 20 mmol of adipic acid, (v) 39 mmol of 2-ethylsuccinic acid, (vi) 45 ml of acetic acid.

The mixture was maintained at 230° C. and at 50 bar of CO (total pressure at this temperature) for 5 h, with stirring.

On distillation as in Example 1, 3 mmol of anhydride corresponding to 2-ethylsuccinic acid were obtained.

EXAMPLE 6

The following reagents were successively introduced into a 125 ml autoclave:

(i) 0.8 mmol of IrCl(cod)$_2$, (ii) 1.6 mmol of HI (at a concentration of 57% in water), (iii) 9 mmol of water (provided by the HI solution)., (iv) 20 mmol of adipic acid, (v) 39 mmol of 2-methylglutaric acid, (vi) 45 ml of acetic acid.

The mixture was maintained at 230° and at 50 bar of CO (total pressure at this temperature) for 5 h, with stirring.

On distillation as in Example 1, 3 mmol of anhydride corresponding to 2-ethylsuccinic acid were obtained (via isomerization of the 2-methylglutaric acid into 2-ethylsuccinic acid).

EXAMPLE 7

50 mmol of 2-methylglutaric acid and 11.6 g of a solution from a trial hydroxycarbonylation of 3-pentenoic acid and containing:

(i) 0.0386 mmol of Ir in soluble form, (ii) 0.0907 mmol of HI, (iii) 3.6 mmol of gamma-valerolactone, (iv) 67 mmol of pentenoic acid, (v) 23.6 mmol of adipic acid, (vi) 6 mmol of 2-methylglutaric acid, and (vii) 1.8 mmol of 2-ethylsuccinic acid, were successively introduced into a 50 ml glass round-bottomed flask.

The mixture was maintained at 130° C. for 30 minutes and then at 200° C. for 2 h, with stirring.

On distillation as in Example 1, 4.5 mmol of anhydride corresponding to 2-methylglutaric acid and 1.8 mmol of the anhydride corresponding to 2-ethylsuccinic acid were obtained.

EXAMPLE 8

10 g of a solution containing:

(i) 0.016 mmol of Ir in soluble form, (ii) 28 mmol of pentenoic acid, (iii) 8.2 mmol of adipic acid, (iv) 37.7 mmol of 2-methylglutaric acid, and (v) 3.4 mmol of 2-ethylsuccinic acid, were introduced into a 50 ml glass round-bottomed flask.

The mixture was heated at 220° C for 90 min, under reduced pressure (430 Pa).

On analysis, it was determined that 23% of the 2-methylglutaric acid and 100% of the 2-ethylsuccinic acid were converted into their respective anhydrides, a considerable fraction of which was distilled off during the anhydridization reaction.

EXAMPLE 9

10 g of a solution containing:

(i) 0.026 mmol of Ir in soluble form, (ii) 41 mmol of pentenoic acid, (iii) 17.1 mmol of adipic acid, (iv) 19.2 mmol of 2-methylglutaric acid, (v) 4.1 mmol of 2-ethylsuccinic acid, and (vi) 24 mmol of acetic anhydride, were introduced into a 50 ml glass round-bottomed flask.

The mixture was heated at reflux (about 120° C.) for 60 min, followed by distillation at 1,300 Pa, up to a temperature of 220° C. in the reaction mixture.

On analysis, it was determined that 99% of the 2-methylglutaric acid and 99% of the 2-ethylsuccinic acid were converted and distilled off.

EXAMPLE 10

The following reagents were introduced into a 500 ml glass round-bottomed flask:

(i) 200 mmol of adipic acid, (ii) 200 mmol of 2-methylglutaric acid, (iii) 250 ml of meta-xylene, (iv) 10 mmol of sulfuric acid.

The mixture was heated, with stirring, at the reflux temperature of the xylene for 4 h and the water formed was distilled off in an azeotropic column (100% of the theoretical amount).

Distillation of the dehydrated mixture separated the 2-methylglutaric anhydride formed (90 mol % relative to the 2-methylglutaric acid charged).

EXAMPLE 11

A mixture containing 15 g (103 mmol) of 2-methylglutaric acid, 2 g (13.7 mmol) of 2-ethylsuccinic acid and 10 g (68.5 mmol) of adipic acid was introduced into a 50 ml glass round-bottomed flask.

The mixture was stirred, heated at 120° C. and maintained at this temperature for 2 hours. It was then maintained at 160° C. under reduced pressure (1,400 Pa) for 6 hours.

On analysis of the distillate obtained, it was determined that 2.2% of the 2-methylglutaric acid and 93% of the 2-ethylsuccinic acid were distilled off in the form of their respective corresponding anhydrides.

EXAMPLE 12

A mixture containing 15 g (103 mmol) of 2-methylglutaric acid, 2 g (13.7 mmol) of 2-ethylsuccinic acid and 10 g (68.5 mmol) of adipic acid, as well as 3 g of sulfonated resin marketed under the trademark Nafion NR 50 (10–35 mesh), was introduced into a 50 ml glass round-bottomed flask.

The mixture was stirred, heated at 120° C. and maintained at this temperature for 2 hours. It was then maintained at 160° C. under reduced pressure (1,400 Pa) for 6 hours.

On analysis of the distillate obtained, it was determined that 4% of the 2-methylglutaric acid and 99% of the 2-ethylsuccinic acid were distilled off in the form of their respective corresponding anhydrides.

EXAMPLE 13

A mixture containing 15 g (103 mmol) of 2-methylglutaric acid, 2 g (13.7 mmol) of 2-ethylsuccinic acid and 10 g (68.5 mmol) of adipic acid, as well as 3 g of KSF montmorillonite acidic clay, was introduced into a 50 ml glass round-bottomed flask.

The mixture was stirred, heated at 120° C. and maintained at this temperature for 2 hours. It was then maintained at 160° C. under reduced pressure (1,400 Pa) for 6 hours.

On analysis of the distillate obtained, it was determined that 24% of the 2-methylglutaric acid and 92% of the 2-ethylsuccinic acid were distilled off in the form of their respective corresponding anhydrides.

EXAMPLE 14

The following reagents were successively introduced into a 125 ml autoclave:

(i) 0.9 mmol of $PdCl_2$, (ii) 7 mmol of chlorobutene, (iii) 92.5 mmol of water, (iv) 92.5 mmol of butadiene, (v) 10 mmol of 3-pentenoic acid, (vi) 34 mmol of adipic acid, (vii) 68.5 mmol of 2-methylglutaric acid.

The mixture was maintained at 100° C under 200 bar of CO (total pressure at this temperature) for 5 h 30, with stirring.

On distillation as in Example 1, 13 mmol of the anhydride corresponding to 2-methylglutaric acids and 1 mmol of the anhydride corresponding to 2-ethylsuccinic acid were obtained.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the separation of at least a fraction of at least one branched, saturated aliphatic diacid having 6 carbon atoms from an admixture thereof with at least adipic acid, comprising at least partially converting said at least one aliphatic diacid in said admixture in the presence of a homogeneous acid catalyst soluble in said admixture and having a pKa less than or equal to 5, or in the presence of a heterogeneous acid catalyst into a corresponding anhydride thereof, and removing said corresponding anhydride or said adipic acid from said admixture.

2. The process as defined by claim 1, wherein said at least one aliphatic diacid is 2-methylglutaric acid, ethylsuccinic acid, dimethylsuccinic acid, or mixtures thereof.

3. The process as defined by claim 1, comprising at least partially converting said at least one aliphatic diacid by heating said admixture to a temperature equal to or greater than 60° C.

4. The process as defined by claim 3, comprising heating said admixture at a temperature ranging from 80° C to 350° C.

5. The process as defined by claim 1 carried out in the presence of a catalytically effective amount of a compound selected from the group consisting of sulfuric acid, hydriodic acid, para-toluenesulfonic acid, trifluoroacetic acid, trifluoromethanesulfonic acid, boron phosphate, zirconia, a sulfonated resin, a smectite, a montmorillonite, a beidellite, a nontronite, a hectorire, a stevensite, and a saponite.

6. The process as defined by claim 1, wherein said admixture prior to said converting step further comprises at least one anhydride having a boiling point less than that of adipic acid.

7. The process as defined by claim 6, said at least one anhydride being an anhydride of a monocarboxylic or polycarboxylic acid having from 2 to 8 carbon atoms.

8. The process as defined by claim 7, said at least one anhydride is acetic acid, propionic acid, succinic acid, valeric acid, 2-ethylsuccinic acid, dimethylsuccinic acid, a methylbutanoic acid, a methylbutenoic acid, a pentenoic acid, or a mixed anhydride thereof.

9. The process as defined by claim 6, wherein the molar ratio of said at least one anhydride/diacids to be anhydridized ranges up to 10.

10. The process as defined by claim 1, said admixture originating from the recovery of the at least one diacid in recrystallization waters of adipic acid.

11. The process as defined by claim 10, said admixture originating from the distilland of the distillation of said at least one diacid.

12. The process as defined by claim 10, said admixture originating from a fraction of crystallization, refining or distillation in a synthesis of adipic acid.

13. The process as defined by claim 1, said admixture originating from the synthesis of adipic acid.

14. The process as defined by claim 13, said admixture comprising adipic acid and 2-methylglutaric acid, 2-ethylsuccinic acid, dimethylsuccinic acid, or mixtures thereof; said admixture being obtained from the hydroxycarbonylation of pentenoic acids, or from the hydroxycarbonylation of butadiene or derivatives thereof, and optionally comprising greater or lesser amounts of the catalyst employed therefor.

15. The process as defined by claim 1, said admixture further comprising a solvent.

16. The process as defined by claim 15, wherein said solvent is an aliphatic or cycloaliphatic hydrocarbon, a halogenated aliphatic or cycloaliphatic hydrocarbon, an aromatic hydrocarbon, a halogenated aromatic hydrocarbon, an aliphatic or aromatic or mixed ether, a carboxylic acid, or a halogenated carboxylic acid.

17. The process as defined by claim 16, wherein said solvent is benzene, toluene, a xylene, n-hexane, dichloromethane, 1,2-dichloroethane, cyclohexane, chlorobenzene, diphenyl ether, dibutyl ether, a pentenoic acid, valeric acid, gamma-valerolactone, acetic acid, propionic acid, or trifluoroacetic acid.

18. The process as defined by claim 1, comprising distilling said corresponding anhydride from said admixture, either contemporaneously with or subsequent to the converting step.

19. The process as defined by claim 1, comprising removing said corresponding anhydride by crystallization.

20. The process as defined by claim 1, wherein the molar ratio of said acid catalyst/diacids to be anhydridized ranges up to 10.

21. The process as defined by claim 20, said molar ratio ranging from 0.0005 to 1.

22. The process as defined by claim 1, wherein the converting step is carried out in the presence of an acidic clay catalyst, in a weight ratio of said acidic clay catalyst/diacids to be anhydridized of at least 5%.

* * * * *